United States Patent [19]

Kaplan et al.

[11] 4,360,600
[45] Nov. 23, 1982

[54] PROCESS FOR PRODUCING ETHYLENE GLYCOL AND METHANOL

[75] Inventors: Leonard Kaplan, Dunbar, W. Va.; Robert G. Bergman, Kensington, Calif.

[73] Assignee: Union Carbide Corporation, Danbury, Conn.

[21] Appl. No.: 278,899

[22] Filed: Jun. 29, 1981

[51] Int. Cl.$^3$ .................................... C07C 27/06
[52] U.S. Cl. ............................ 518/700; 252/431 R
[58] Field of Search .......................... 518/700, 715

[56] References Cited

U.S. PATENT DOCUMENTS 2,535,060 12/1950 Gresham .............................. 518/715
2,549,470 4/1951 Howk et al. ......................... 518/715
2,632,014 3/1953 Gresham .............................. 518/715

FOREIGN PATENT DOCUMENTS 1573422 8/1980 United Kingdom ................ 518/700

Primary Examiner—Howard T. Mars
Attorney, Agent, or Firm—Gary L. Wamer

[57] ABSTRACT

This invention relates to the manufacture of ethylene glycol, methanol, and derivatives thereof from the reaction of hydrogen and oxides of carbon, by a homogeneous catalytic process using as the catalyst a solubilized ruthenium carbonyl complex and an organosilicon compound having a hydrogen bonded to silicon (—Si—H).

10 Claims, No Drawings

PROCESS FOR PRODUCING ETHYLENE GLYCOL AND METHANOL

BACKGROUND OF THE INVENTION

This invention relates to an improved process, and the catalyst which achieves this process, for making ethylene glycol and methanol directly from synthesis gas, i.e., mixtures of hydrogen and oxides of carbon. More particularly, this invention achieves the production of ethylene glycol and methanol directly from synthesis gas in the presence of a catalyst which is a ruthenium carbonyl complex and an organosilicon compound having a hydrogen bonded to silicon under process conditions which heretofore were regarded as being incapable of producing ethylene glycol and methanol with a ruthenium containing catalyst.

Ruthenium has been explored as a catalyst by many. It has been considered as a hydrogenation catalyst, as a hydroformylation catalyst, as a catalyst to produce a wide range of monohydric alcohols (non-specific as to any of them) exclusive of methanol, as an alcohol homologation catalyst such as for the conversion of methanol to ethanol,* and as a high pressure catalyst to selectively produce methanol and methyl formate.

*See, for example, U.S. Pat. Nos. 4,133,966 and 3,285,948; and Japanese Patent Application (Kokai) No. 52-73804/77 (June 21, 1977) [Application No. 50-149391/75 (application date, Dec. 15, 1975)] to Mitsubishi Gas Chemical Industry Company.

In Gresham, U.S. Pat. No. 2,535,060, there is described a process for preparing monohydric alcohols by introducing carbon monoxide, hydrogen and a hydroxylated solvent into a reaction vessel and heating the mixture in the presence of a ruthenium-containing substance and an alkaline reagent which controls the pH within the range of 7 to 11.5, at a temperature within the range of 150° to 300° C. under a pressure within the range of 200 to 1,000 atmospheres.

Solid ruthenium dioxide is used in Examples 1 and 2 of the Gresham patent. At column 2, lines 30-33 of the patent, the patentee states his belief that ruthenium dioxide is reduced in situ during the reaction. Example 1 compares the use of a number of solutes such as phosphoric acid, acidic phosphate buffer, no solutes at all, ammonia and sodium bicarbonate. In this example, the solvent was water. In Example 2 of Gresham, a number of alcohols were characterized as solvents.

Gresham states that ruthenium and its compounds are "specific" in their effect upon this reaction and other catalysts "do not lead to straight chain primary alcohols under the conditions of this process". There is no indication that Gresham's process, as operated by him, produced ethylene glycol.

Gresham's work should be contrasted with his earlier work described in U.S. Pat. No. 2,636,046, filed Oct. 16, 1948. In this patent, Gresham describes the production of polyfunctional oxygen-containing organic products including such compounds as ethylene glycol, glycerine, and the like.*

*Note Rathke and Feder, JACS, 100, pp. 3623-3625 (May 24, 1978); Ann. N.Y. Acad. Sci., 333, 45 (1980).

This is accomplished by the reaction of hydrogen with carbon monoxide in the presence of a solvent to produce glycol. According to this patent, the reaction of carbon monoxide with hydrogen must be at pressures of above 1,000 atmospheres and "particularly above a minimum of about 1,400 atmospheres" in order to obtain the "polyfunctional oxygen-containing organic compounds . . . in excellent yield" (column 2, lines 9-17). The patent specifically states at column 2, lines 37-43, that "[I]n the hydrogenation of oxides of carbon at pressures of 1,000 atmospheres and below, virtually no polyfunctional compounds are produced. At pressures above 1,000 atmospheres and especially at pressures of about 1,500 to 5,000 atmospheres preferably 2,000 to 5,000 atmospheres, polyfunctional compounds are obtained."

Though the examples of the patent describe the use only of cobalt catalyst, the patentee, at column 3, line 61, indicates that the catalyst may contain "cobalt, ruthenium, etc." According to the patentee, the most outstanding results are obtained by using a catalyst containing cobalt, especially compounds of cobalt which are soluble in at least one of the ingredients of the reaction mixture.

Prior to the filing of U.S. Pat. No. 2,535,060 and subsequent to the filing of U.S. Pat. No. 2,636,046, there was filed on Apr. 12, 1949, a commonly assigned application by Howk, et al. which issued as U.S. Pat. No. 2,549,470 on Apr. 17, 1951. The Howk, et al. patent is directed to a catalytic process for making monohydric straight chain alcohols and does not mention the production of ethylene glycol. The patent emphasizes the production of straight chain primary hydroxyalkanes having from 3 to 50 or more carbon atoms in the molecule. This, the patent states, is accomplished by introducing hydrogen, carbon monoxide and a hydroxylated solvent into a reaction vessel, and heating the mixture in the presence of a catalyst of the class consisting of ruthenium metal, ruthenium oxide and ruthenium carbonyl, at a pressure within the range of 200 to 1,000 atmospheres and at a temperature within the range of 100° to 250° C. The liquid hydroxyl-containing reaction medium may be water or alcohol, preferably a primary hydroxyalkane having from 1-10 carbon atoms per molecule. According to the patentee, a substantial proportion of the reaction product usually consists of alcohols containing more than 6 carbon atoms per molecule. The patent goes on to state (column 1, line 50, et seq.):

"The reaction products usually contain virtually no hydrocarbons, acids, esters, or branched-chain alcohols. These results were entirely unexpected, in view of the existing knowledge of the catalytic reaction between carbon monoxide and hydrogen in the presence of alcohols and Group VIII metal catalysts."

According to the Howk, et al. patent:

"It should be emphasized here that, under the conditions of temperature, pressure and gas ratios just described, no reaction takes place between carbon monoxide and hydrogen in a liquid medium (water or alcohol) if one of the common group VIII metals, such as cobalt or nickel, is used as the catalyst. This is evidenced by the fact that, using, for example, a cobalt catalyst, no significant drop in pressure is observed when carbon monoxide and hydrogen are contacted under the conditions recited. Ruthenium is thus unexpectedly different from these related metals." (Column 4, lines 19-30.)

The numbered examples indicate an apparent preference for making normal-monohydric alcohols, with the proportion of pentane soluble to pentane insoluble alcohol being at least 2:1. In one example, starting at the bottom of column 6 of Howk, et al., the solvent employed is characterized as a carboxylic acid or anhydride rather than the neutral hydroxylated solvents which were described in the other examples. This comparative example demonstrated that in a process operated at 200° C. for 18 hours using pressures maintained in the range of 300-950 atmospheres by repressurizing periodically with synthesis gas, there was produced a reaction product containing "a large quantity of wax." According to the author, 40.55 parts of esters boiling from 59° C. at atmospheric pressure to 150° C. at 116 millimeters pressure were obtained and this can be compared to the wax obtained in the amount of 37.06 parts. In that particular example, the patentee appears to have demonstrated that when one does not employ the hydroxylated solvent, the amount of wax essentially equals the amount of pentane soluble alcohol products obtained. This is supported by the statement at column 2 of Gresham U.S. Pat. No. 2,535,060 which refers to Howk, et al. Ethylene glycol diacetate is also observed.

At column 3, lines 54 et seq., Howk, et al. describe the influence that pressure has on the course of the reaction. According to Howk, et al. with pressures up to about 150 atmospheres the reaction products are only hydrocarbons. This appears to be in accord with recent work described by Masters, et al. in German Patent Application (Offenlegungsschrift) No. 2,644,185*, based upon British priority application Specification No. 40,322-75, filed Oct. 2, 1975. Masters, et al. obtained only hydrocarbons at such pressures using a ruthenium catalyst.
*See Doyle, et al., *J. of Organometallic Chem.*, 174 C55–C58 (1979), who conclude that the process characterized in the German Offenlegungsschrift involved a heterogeneous Fischer-Tropsch reaction.

Fenton, U.S. Pat. No. 3,579,566, patented May 18, 1971, is concerned with a process of reducing organic acid anhydrides with hydrogen in the presence of a Group VIII noble metal catalyst and a biphyllic ligand of phosphorus, arsenic or antimony. The process of Fenton bears a remarkable similarity to oxo processing conditions to produce aldehydes and alcohols (compare with Oliver, et al., U.S. Pat. No. 3,539,634, patented Nov. 10, 1970) except that Fenton fails to supply an olefinic compound to the reaction. In the Fenton reaction, an acid anhydride, such as acetic acid anhydride, is reduced to ethylidene diacetate in the presence of hydrogen or $CO/H_2$ and a rhodium halide or a mixture of palladium chloride and ruthenium trichloride catalyst, provided in combination with triphenylphosphine. Ethylene glycol diacetate is also observed. Of particular significance is the fact that none of Fenton's examples produce a methyl ester, as are produced by the process of co-pending U.S. patent application Ser. No. 971,667, discussed below and encompassed herein. Another point is that it is possible that Fenton's ethylidene diacetate can be converted to ethylene glycol diacetate under the conditions of example 1.

W. Keim, et et., (Journal of Catalysis, 61, 359 (1980) has reported that reaction of $Ru_3(CO)_{12}$ under very high pressures (2,000 bars) produce mainly methanol and methyl formate, but traces of glycol (0.8 to 1.2 percent of the total products) were also seen. In one experiment a small amount of ethanol was detected. No glycerine was observed in these reactions.

Pruett and Walker, U.S. Pat. No. 3,833,634, patented Sept. 3, 1974, based on an application originally filed Dec. 21, 1971, describe a process for preparing glycols by reacting an oxide of carbon with hydrogen using a rhodium carbonyl complex catalyst. The examples of the patent compare the reaction of hydrogen and carbon monoxide in the presence of the desired rhodium containing catalyst and other metals. In Example 9 of the patent, the reaction was attempted with triruthenium dodecacarbonyl as the catalyst using tetrahydrofuran as the solvent with a reaction temperature of 230° C. for 2 hours, and "the product contained no polyhydric alcohol."

According to Roy L. Pruett, *Annals, New York Academy of Sciences*, Vol. 295, pages 239–248 (1977), at page 245, metals other than rhodium were tested to determine the production of ethylene glycol from mixtures of carbon monoxide and hydrogen. These metals include cobalt, ruthenium, copper, manganese, iridium and platinum. Of these metals, only cobalt was found to have a slight activity, citing British Pat. No. 665,698 which corresponds generally to the last mentioned Gresham U.S. patent. Pruett stated that such slight activity with cobalt was "qualitatively" in agreement with the results obtained by Ziesecke, 1952, Brennstoff-Chem, 33:385.

In a recent report (Journal of the American Chemical Society, vol. 101, pp.7419–21 (1979)) J. S. Bradley of Exxon Corporation produced methanol and methyl formate at a selectivity greater than 99% without hydrocarbon products detected, by the reaction of sythesis gas ($H_2:CO=3:2$) under pressures on the order of 1,300 atmospheres and at temperatures around 270° C. using a Ru catalyst. J. S. Bradley (in "Fundamental Research in Homogeneous Catalysis", ed. M. Tsutsui, vol. 3, Plenum Press, 1979, pages 165 et seq.) discusses the formation of ethylene glycol as reported by Gresham and reports the hydrogenation of carbon monoxide to methanol and methyl formate in the presence of ruthenium carbonyl clusters and under a pressure of about 1300 atmosphere. Bradley concluded at page 175, stating that, "On the basis of these results it seems that claims of homogeneous catalysis of hydrocarbon formation by $Ru_3(CO)_{12}$ in solution are probably erroneous."

An interesting exception to the previously report inactivity of ruthenium catalysts to produce glycol is the high pressure (viz. 1650–1750 bars) experiment reported by R. Fonseca, et al., High Pressure Science and Technology, 6th AIRAPT Conference (Chapt. "High Pressure Synthesis of Polyalcohols by Catalytic Hydrogenation of Carbon Monoxide"), pages 733–738 (1979), published by Plenum Press, New York. In this experiment, the authors report the reaction in tetraglyme of a $CO:H_2$ (1:2 ratio) mixture at 1650–1765 bars, i.e., about 25,000 psi (1,757.6 $kg/cm^2$) and at 230° C. using triruthenium dodecacarbonyl and 2-pyridinol as a ligand, both in unstated amounts, for a period of 5 hours. The authors report a % conversion of 12.9 (unstated basis), a % yield of polyols of 3 (unstated basis), and % selectivities as follows: ethylene glycol, 22.9 percent; glycerine, 0; and methanol, 16.1 percent. This work was investigated recently and reported by G. Jenner et al., React. Kinet. Catal. Lett., Vol. 15, No. 1 103–112 (1980). The authors therein concluded that ethylene glycol was absent when a $Ru_3(CO)_{12}$ catalyst was employed. Further, in Williamson, et al., U.S. Pat. No. 4,170,605, patented Oct. 9, 1979, the patentees report in Examples I and II the reaction in 1-propanol of synthesis gas ($CO:H_2=1:1$) at 25,000 psig and at 230° using ruthenium tris (acetylacetonate) and 2-hydroxypyridine, the latter being the same ligand employed by Fonseca et al., supra, for a period of 2 and 3 hours, respectively. In Example I, Williamson, et al. report the production of 4 grams of product* containing (mole percent basis): ethylene glycol, 57% and methanol, 25%. In Example II, 7 grams of product* are reported containing 66 and 16 mole percent of ethylene glycol and methanol, respectively.

*Included in the 4 and 7 grams of product are trace amounts of water and methylformate, as well as 16 mole % (Example I) and 15 mole % (Example II) of propylformate. The latter compound would appear to be derived from 1-propanol initially present in the reaction mixture, rather than a synthesis gas-derived product.

Deluzarche, et al., *Erdol and Kohle-Erdgas-Petrochemie*, Bd. 32, Heft 7, July 1979, pp. 313–316, discloses that pressures over 25,000 psi produce methanol and ethylene glycol from synthesis gas in the presence of a $Ru_3(CO)_{12}$ catalyst.

Further, in copending application Ser. No. 091,242, filed Nov. 15, 1979, there is described a process for selectively producing methanol, ethanol, and ethylene glycol by reacting carbon monoxide and hydrogen in a homogeneous liquid phase mixture containing a ruthenium carbonyl complex. The reaction is effected at a temperature between about 50° C. to about 400° C. and a pressure of between about 500 psia (35.15 kg/cm$^2$) and about 15,000 psia (1,054.6 kg/cm$^2$) for a period of time sufficient to produce such products; and in copending application Ser. No. 971,750, filed Dec. 21, 1978, there is described an improved process for producing methyl and ethylene glycol esters as described in Ser. No. 091,242 in which the improvement comprises maintaining the combined concentration of methyl ester, ethylene glycol ester and water in the reaction medium at less than about 30 vol.%.

There is disclosed in U.S. patent application Ser. No. 921,698, filed July 3, 1978, in the name of John. F. Knifton, assigned to Texaco Development Corp., a process for the production of alcohol and vicinal glycol esters from synthesis gas by reacting such synthesis gas in a carboxylic acid medium in the presence of a ruthenium catalyst at a temperature of between 100° C. and 350° C. and superatmospheric pressures of 500 psia or greater. In this particular application a co-catalyst species is employed with the ruthenium catalytic species. The co-catalyst is selected from the group consisting of alkali metal salts, alkaline earth salts, quaternary ammonium salts, iminium salts and quaternary aliphatic phosphonium salts.

In U.S. patent application Ser. No. 921,699, filed July 3, 1978 by Knifton, a similar process is described in which the catalyst contains either ruthenium or osmium. However, in this particular application the carboxylates of ethylene glycol are formed without the utilization of a co-catalyst. Essentially the same or similar disclosure as set forth in the aforementioned two patent applications can be found in U.S. Ser. No. 967,943, filed Dec. 11, 1978, and U.S. Pat. No. 4,268,689 which issued. The disclosures of the aforementioned four patent applications can be found in British Patent Publication No. 2,024,811.

U.S. Pat. No. 4,265,828 discloses a process for making ethylene glycol by contacting a mixture of carbon monoxide and hydrogen with a ruthenium-containing compound dispersed in a low melting quaternary phosphonium or ammonium base or salt under a pressure of 500 psi or greater at a temperature of at least 150° C.

The preparation of vicinal glycol ester, e.g., ethylene glycol acetate esters, by the reaction of synthesis gas in the presence of an aliphatic carboxylic acid and a homogeneous ruthenium catalyst is further discussed by J. Knifton, J.C.S., Chem. Comm, page 188 (1981). The ruthenium catalyst precursor is preferably a ruthenium compound in combination with a large cationic species, such as a quaternary phosphonium or quaternary ammonium salts. The presence of the large cationic species was considered to aid in stabilizing an anionic ruthenium cluster during the carbon monoxide hydrogenation sequence.

The hydrogenation of carbon monoxide to methanol and ethylene glycol in the presence of a homogeneous ruthenium catalyst to form ethylene glycol with acetic acid solutions is discussed by B. Duane Dombek, J.Am. Chem. Soc., 102, 6855 (1980). The reaction is reported to produce substantial quantities of methyl acetate, smaller amounts of ethylene glycol diacetate and traces of glycerine triacetate.

In copending application U.S. Ser. No. 278,900, filed concurrently herewith, a process is disclosed for the manufacture of ethylene glycol, methanol, and derivatives thereof from the reaction of hydrogen and carbon monoxide, by a homogeneous catalytic process using as the catalyst a cobalt containing compound and an organosilicon compound having a hydrogen bonded to silicon (—Si—H).

In copending application U.S. Ser. No. 278,878, filed concurrently herewith, a process is disclosed for the manufacture of alcohols and derivatives thereof from the carbon residue of an organosilicon compound wherein such alcohol has one carbon more than the corresponding carbon residue from which it was derived.

As pointed out above, ethylene glycol can be produced directly from a mixture of hydrogen and carbon monoxide using a rhodium carbonyl complex as a catalyst. There has been a substantial amount of work done on the formation of ethylene glycol from mixtures of hydrogen and carbon monoxide in the presence of rhodium carbonyl clusters, such as is disclosed in U.S. Pat. Nos. 3,833,634; 3,878,214; and 3,878,290.

The above discussion provides a characterization of technology heretofore published or filed upon which relates to the direct production of ethylene glycol from mixtures of carbon monoxide and hydrogen or the production of monohydric alcohols from the direct reaction of hydrogen and carbon monoxide in the presence of a ruthenium catalyst.

Owing to the reduced availability of petroleum sources the cost of producing chemicals from petroleum has been steadily increasing. Many have raised the dire prediction of significant oil shortages in the future. Obviously a different low cost source is needed which can be converted into the valuable chenicals now derived from petroleum sources. Synthesis gas is one such source which can be effectively utilized in certain circumstances to make chemicals.

The most desirable aspect of synthesis gas is that it can be produced from non-petroleum sources. Synthesis gas is derived by the combustion of any carbonaceous material including coal, or any organic material, such as hydrocarbons, carohydrates and the like. Synthesis gas has for a long time been considered a desirable starting material for the manufacture of a variety of chemicals and, as discussed hereinabove, homogeneous ruthenium catalysts will produce ethylene glycol and methanol directly from synthesis gas.

However, while previously known processes using homogeneous ruthenium catalysts will produce ethylene glycol and other polyhydric alcohols generally very high pressure are required and it would be desirable to produce ethylene glycol and methanol or derivatives thereof at high process efficiency and low or moderate pressures.

SUMMARY OF THE INVENTION

In accordance with the present invention there is provided a process for preparing ethylene glycol, methanol, and derivatives thereof which comprises reacting a mixture comprising oxides of carbon and hydrogen in the presence of a catalytically effective amount of a ruthenium carbonyl complex and an organosilicon compound having at least one silicon atom bonded to hydrogen (—Si—H).

It has been found that when ethylene glycol and methanol were prepared in accordance with the present invention that the production of ethylene glycol, methanol and derivatives thereof can be achieved under pressure and temperature conditions not possible when only a ruthenium carbonyl complex catalyst is employed.

DESCRIPTION OF THE INVENTION

This process constitutes a relatively low pressure process for converting synthesis gas to ethylene glycol, methanol, and derivatives thereof. The process of this invention is carried out with the ruthenium carbonyl complex catlayst and organosilicon compound in solution, even though the ruthenium carbonyl complex may exist during the reaction in more than one liquid phase. In this sense, the reaction is termed a homogeneous liquid phase reaction. There may be more than one such phase existing in the reaction zone but the catalyst is always dissolved in at least one of such phases and is always in a dissolved liquid state.

The process of this invention involves the reaction of synthesis gas in the presence of soluble ruthenium complexes and the organosilcon compound at temperatures and pressures for a period of time sufficient to produce ethylene glycol, methanol, and derivatives thereof under such conditions as set forth herein. The reaction conditions comprise (i) a period of time at a temperature and pressure which cause the hydrogen and oxides of carbon, e.g. carbon monoxide, to react to produce the desired product, (ii) a temperature between about 50° C. and 400° C. and (iii) a pressure between 100 psia (7.0 kg/cm$^2$) and 15,000 psia (1,054.6 Kg/cm$^2$), preferably between about 500 psia (35.15 Kg/cm$^2$) and 12,500 psia (878.4 Kg/cm$^2$). The catalyst of this invention is a ruthenium containing carbonyl complex and a organosilicon compound, having at least one Si—H bond, which under the prescribed reaction conditions catalyzes the aforementioned reaction between carbon monoxide and hydrogen.

The process of this invention is distinctive in the selection of materials which comprise the homogeneous liquid phase mixture, the reaction parameters and the stability of the ruthenium containing catalyst in most cases, indeed, in all cases studied. As with any technology, this process has undergone evolutionary changes and its further examination will undoubtedly bring more changes, most likely in the form of additional or substitutional steps and/or materials.

Apart from the conditions of the reaction in terms of time, temperature and pressure, the selection of solvent may constitute an important consideration in the most advantageous practice of this invention. The selection of solvents is not narrowly limited. The solvent, when employed, is selected such that the solvent is capable of maintaining the ruthenium carbonyl complex catalyst in the homogeneous liquid phase mixture throughout the reaction.

The catalyst of this invention is a ruthenium carbonyl catalyst which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introducted to the reaction in a condition which allows them to be solubilized, and under the conditions of the reaction they are converted into a carbonyl complex which effectively catalyzes. Factors achieving the catalyst are the reaction parameters and the choice of solvent. Varied reaction conditions and solvents may result in different amounts of the desired products of the process, and different rates, efficiencies and/or yields.

The ruthenium-containing substances which may be employed in the practice of this invention to form the catalyst encompass those which are described, for example, in Gresham, U.S. Pat. No. 2,535,060 at column 2, starting at line 38 to line 48, and ruthenium carbonyl compounds. It generally is not advisable to place ruthenium compounds or substances on a support material for use in the process of this invention because such offers no benefits over solubilizing such ruthenium compounds in combination with the aforementioned solvent. Moreover, ruthenium deposited on a support material can be expected to be solubilized in the homogeneous liquid phase reaction system of this invention as it is contacted with carbon monoxide. Ruthenium oxides, such as dioxide, sesquioxide, or tetraoxide, may be converted to the ruthenium carbonyl complex employed in the process of this invention. Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than othe ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide a readily available source of ruthenium for the ruthenium carbonyl catalyst of this process.

The selection of the organosilicon compound, i.e. silane, is such that the organo silicon compound contains at least one bond between a silicon atom and a hydrogen atom. Typical of suitable organosilicon compounds are alkyl silanes, mono-, di- and tri- alkyl silanes, e.g. trihexylsilane, wherein said alkyl substituents may be substituted. In general the organosilicon compound is selected such that at least one hydrogen bonded to silicon is present in the organosilicon compound. Thus, silane compounds, including silicon derived polymers, having at least one silicon to hydrogen bond may be employed in the instant process. Representative compounds which are suitable for use in the instant process are set forth in E. Wiberg and E. Amberger, "Hydrides of Elements of Main Groups I-IV", Elsevier, 1971, pages 462-638; and V. Bazant and V. Chvalovsky, "Chemistry of Organosilicon Compounds," vol. 1 of V. Bazant, V. Chvalovsky, and J. Rathousky, "Organosilicon Compounds," Academic Press, 1965, p. 102-151, said disclosures to said suitable organosilicon compounds being incorporated by reference herein. Typical of such organosilicon compounds are as follows:

$SiH_4$
$H_3SiCH_2SiH_3$
$H_3SiCH_2CH_2SiH_3$
$CH_3SiH_2CH_2SiH_3$
$CH_3SiH_2CH_2SiH$ $CH_3SiH_2CH_2SiH_2$
|
$CH_3SiH_2CH_2$

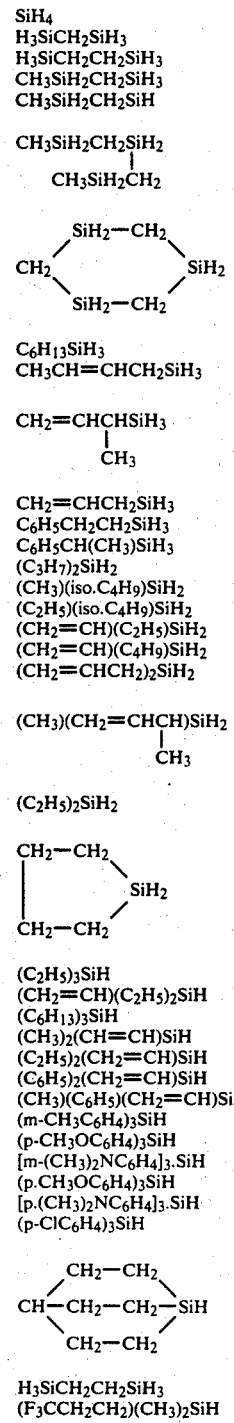

$C_6H_{13}SiH_3$
$CH_3CH=CHCH_2SiH_3$ $CH_2=CHCHSiH_3$
|
$CH_3$ $CH_2=CHCH_2SiH_3$
$C_6H_5CH_2CH_2SiH_3$
$C_6H_5CH(CH_3)SiH_3$
$(C_3H_7)_2SiH_2$
$(CH_3)(iso\text{-}C_4H_9)SiH_2$
$(C_2H_5)(iso\text{-}C_4H_9)SiH_2$
$(CH_2=CH)(C_2H_5)SiH_2$
$(CH_2=CH)(C_4H_9)SiH_2$
$(CH_2=CHCH_2)_2SiH_2$ $(CH_3)(CH_2=CHCH)SiH_2$
|
$CH_3$ $(C_2H_5)_2SiH_2$ $(C_2H_5)_3SiH$
$(CH_2=CH)(C_2H_5)_2SiH$
$(C_6H_{13})_3SiH$
$(CH_3)_2(CH=CH)SiH$
$(C_2H_5)_2(CH_2=CH)SiH$
$(C_6H_5)_2(CH_2=CH)SiH$
$(CH_3)(C_6H_5)(CH_2=CH)SiH$
$(m\text{-}CH_3C_6H_4)_3SiH$
$(p\text{-}CH_3OC_6H_4)_3SiH$
$[m\text{-}(CH_3)_2NC_6H_4]_3.SiH$
$(p.CH_3OC_6H_4)_3SiH$
$[p.(CH_3)_2NC_6H_4]_3.SiH$
$(p\text{-}ClC_6H_4)_3SiH$

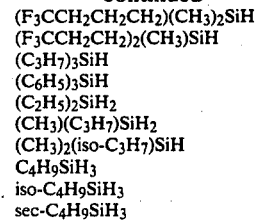

$H_3SiCH_2CH_2SiH_3$
$(F_3CCH_2CH_2)(CH_3)_2SiH$

-continued
$(F_3CCH_2CH_2CH_2)(CH_3)_2SiH$
$(F_3CCH_2CH_2)_2(CH_3)SiH$
$(C_3H_7)_3SiH$
$(C_6H_5)_3SiH$
$(C_2H_5)_2SiH_2$
$(CH_3)(C_3H_7)SiH_2$
$(CH_3)_2(iso\text{-}C_3H_7)SiH$
$C_4H_9SiH_3$
iso-$C_4H_9SiH_3$
sec-$C_4H_9SiH_3$ As characterized above, this process is operated as a homogeneous liquid phase mixture. The process is typically carried out in a solvent although the organosilicon compound may act as the solvent for the catalyst. The solvent may be solid at room temperature but should at least, in part, be a liquid under the conditions of reaction.

Illustrative of suitable solvents are, e.g., ketones, esters including lactones, amides including lactams, sulfones, sulfoxides, aromatic hydrocarbons, and the like. Illustrative of specific solvents encompassed by the above classes of solvents are, for example, aromatic hydrocarbons, e.g., benzene, toluene, xylene, naphthalene, alkylnaphthalene, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam, N-alkyl pyrrolidinones such as N-methyl pyrrolidinone, cyclic ureas such as N,N'-dimethylimidazolidone; lactones such as gamma-butyrolactone; amides such as dimethylformamide, dimethylacetamide, hexamethylphosphoramide; sulfones such as sulfolane, dimethylsulfone, the substituted sulfolanes described in U.S. Pat. No. 4,224,237; sulfoxides such as dimethylsulfoxide, diphenyl sulfoxide; as well as many others.

Illustrative of other suitable solvents are the ethers, and the like. Illustrative of specific solvents encompassed by the above class of solvents are, for example, ethers such as tetrahydrofuran, tetrahydropyran, diethyl ether, 1,2-dimethoxybenzene, 1,2-diethoxybenzene, the dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene; the crown ethers such as described in U.S. Pat. No. 4,162,261, which description of crown ethers, as solvents in that case, are incorporated herein by reference; as well as many others.

In addition, the solvent employed in the practice of this invention may comprise a mixture of two or more of the aforementioned solvents. Which mixtures will achieve what result has not been determined.

The process may be carried out in the presence of a promoter although selection of the promoter is not clearly understood. A promoter, in the context of this invention, is a material provided to the reaction which provides a promotional effect in that it enhances the production (viz., rate, yield, or efficiency) of any of the products, or it improves the selectivity of the reaction toward ethylene glycol rather than methanol or it helps to reduce the loss of ruthenium during the reaction.

Though the process of this invention is capable of providing a combination of ethylene glycol and methanol and derivatives thereof, in many instances one or more of them is formed as a minor component only. Because ethylene glycol is the most valued of the products, its production obviously makes this process attractive. Formation of methanol also enhances the commercial attractiveness of this process.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20, and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention.

The quantity of ruthenium and the quantity of organosilicon catalyst employed are not narrowly critical and can vary over a wide range. In general, the process is desirably conducted in the presence of a catalytically effective amount of each catalyst which gives a suitable and reasonable reaction rate.

The reaction can proceed when employing as little as about $1 \times 10^{-6}$ weight percent, and even lesser amounts, of each catalyst, based on the total weight of reaction mixture (i.e., the liquid phase mixture). The upper concentration limit can be quite high, e.g., about 30 weight percent, and higher of the ruthenium catalyst and up to about 100 percent by weight of the organosilicon catalyst, e.g., when the organosilicon catalyst is also employed as the solvent; the realistic upper limit in practicing the invention appears to be dictated and controlled more by economics in view of the cost of ruthenium. Since the rate of conversion of synthesis gas may be dependent upon the concentration of catalyst employed, higher concentrations achieving higher rates, large concentrations may prove to be a most desirable embodiment of this invention. Depending on various factors such as the partial pressures of carbon monoxide and hydrogen, the total operative pressure of the system, the operative temperature, the choice of solvent, and other considerations, a catalyst concentration of from about $1 \times 10^{-3}$ to about 20 weight percent of the ruthenium catalyst and up to about 100 percent by weight of the organosilicon catalyst, e.g., when the organosilicon catalyst is also employed as the solvent, based on the total weight of reaction mixture, is generally desirable in the practice of the invention. The actual concentration which will provide for the formation of the products will depend on several factors and for a given organosilicon compound under a given set of reaction conditions the concentration may be greater than $1 \times 10^{-3}$ to provide for the formation of product.

The temperature which may be employed in practicing the process may vary over a wide range of elevated temperatures. In general, the process can be conducted at a temperature between 50° C. and about 400° C. and higher. Temperatures outside this stated range, though not excluded from the scope of the invention, do not fall within certain desirable embodiments of the invention.

The examples below depict batch reactions; however, a continuous gas recycle process can be operated in a similar manner. That is, the batch reactor simulates the continuous reactor except for the gas sparging and continuous gas recycle.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and intent of this invention.

EXPERIMENTAL PROCEDURE

The following examples, except for Examples 9 and 10, were carried out according to the following procedure:

A 150 ml. capacity stainless steel reactor capable of withstanding pressures up to 7,000 atmospheres was charged with a premixed amount of 75 cubic centimeters (cc) of an organosilicon compound (for comparative Examples 6-8 the organosilicon compound employed in the instant process was replaced by dibutyl ether, tetraethylsilane or sulfolane, respectively), and a specified amount of a metal compound, as indicated in the examples hereinafter. The reactor was sealed and charged with a gaseous mixture containing equal molar amounts of carbon monoxide and hydrogen to a pressure as specified below. Heat was applied to the reactor and its contents; when the temperature of the mixture inside the reactor reached 190° C., as measured by a suitably placed thermocouple, an additional adjustment of carbon monoxide and hydrogen ($H_2:CO=1:1$) was made to bring the pressure back to that which is specified in the Tables for the examples hereinafter. The temperatures and pressures were maintained as indicated in the examples.

After the reaction was terminated, the vessel and its contents were cooled to room temperature, the excess gas vented and the reaction product mixture was removed. The reactor was then washed with acetone. The reaction mixture and wash were then analyzed by use of vapor phase chromatography (VPC) and nuclear magnetic resonance (NMR).

The reaction mixture (1.0 g of the reaction mixture) was treated with benzoic anhydride (1.46 grams) by placing the reaction mixture and the benzoic anhydride in a glass tube which was then sealed with a rubber septum and a cap. The mixture was shaken and then heated to about 250° C. in an oil bath for about 1 hour. The mixture was then cooled to ambient conditions and dissolved in 3 milliliters of $CDCl_3$ prior to analysis by VPC and NMR. The effects of the concentration of benzoic anhydride, temperature, and reaction time were studied and the aforementioned procedure determined to be a procedure which adequately combines sufficiency and convenience. The results reported in the following examples are based on these analyses, i.e., the results are the amounts of methyl benzoate and glycol dibenzoate detected but are expressed and reported as the methanol and ethylene glycol equivalents. The treatment of the reaction mixture is based on a report [A. Ladenburg, Ber., 5, 319(1872)] of the reaction: $Et_3SiOEt + (CH_3CO)_2O \rightarrow Et_3SiOCOCH_3 + EtOCOCH_3$; ($Et = C_2H_5$).

The effeciency of the treatment of the reaction mixture with benzoic anhydride was studied by heating a representative silane (0.40 gram, 3.2 millimoles, of trimethylethoxysilane) with 0.73 gram of benzoic anhydride at 250° C. for 1 hour in a totally-immersed sealed tube. The NMR spectrum of the reaction mixture indicated a 77 percent conversion to ethyl benzoate. Similarly, $(C_6H_{13})_3$ SiOCH$_2$CH$_2$OSi $(C_6H_{13})_3$ (0.111 g, 0.177 mmole) was heated with 0.73 g of benzoic anhydride in 1.000 g (3.5 mmoles) of trihexylsilane with a 57 percent conversion to glycol dibenzoate observed. In addition, according to the above procedure, 0.112 grams of $(C_6H_{13})_3$ SiOCH$_2$CH$_2$OSi$(C_6H_{13})_3$ and 1.003 grams of trihexylsilane were treated with benzoic anhydride with a 62 percent conversion to glycol dibenzoate observed.

In Examples 9 and 10 the following procedure was employed:

A 150 ml stainless steel reactor capable of withstanding pressures up to 10,000 psig and containing a removal glass liner was charged with a ruthenium compound (as designated below in examples 9 and 10). The reactor was purged with carbon monoxide and pressurized with an initial charge of 500 psig (36.19 Kg/cm$^2$) of carbon monoxide. Carbon monoxide and hydrogen (1:1 mole ratio) were then added to the reactor to attain the desired pressure. The reactor was rocked and the contents heated to the reaction temperature and maintained at the reaction temperature for two hours while rocking the reactor. The pressure was maintained at the specified reaction pressure during the indicated period of the reaction by adding carbon monoxide and hydrogen. With these added repressurizations the pressure inside the reactor was maintained at the reaction pressure over the reaction period. The reactor was then cooled and vented. The contents of the reactor were removed and treated and analyzed by VPC and NMR as above-described.

The preparation of (n-C$_6$H$_{13}$)$_3$ SiOCH$_2$OSi (n-C$_6$H$_{13}$)$_3$ was carried out by reacting ethylene glycol (2.4 grams, 0.039 mole) (stirred with NaOH, then distilled at 92° C./10 mm), trihexylchlorosilane (25 grams, 0.078 mole), and pyridine (7.8 milliliter, 0.097 mole; refluxed over NaOH, then distilled at 113° C. and stored over CaH$_2$) in 47 milliliters of toluene (dried over conventional molecular sieves) according to the procedure described by R. O. Sauer, J. Am. Chem Soc., 66, 1707 (1944) for the preparation of (CH$_3$)$_3$SiOCH$_3$, which reference is incorporated herein by reference. Five grams of the crude product (from a total weight of about 25 grams) was purified by chromatography using 200 grams of Woelm (TM) silica gel. A final product of at least 1.5 grams was obtained. [NMR (CDCl$_3$):3.63 (s, 2.0H), 5.6–7.2 (m, 39H) ppm upfield from CHCl$_3$; Chemical ionization (isobutane) mass spectrum: calculated for C$_{38}$H$_{82}$O$_2$Si$_2$, 626.5853, for C$_{38}$H$_{82}$O$_2$Si$_2$-C$_6$H$_{13}$, 541.4835; found 626.5198±66 ppm (parent), 541.4828±1.3 ppm (base)]

EXAMPLES 1–5

1–5 were carried out according to the above described experimental procedure using 80 milliliter of trihexylsilane which was reacted at 270° C. for 4 hours under an atmosphere of carbon monoxide and hydrogen (1:1 mole) ratio). The pressure employed in each example is set forth in Table I. Examples 1–3 are comparative examples employing only trihexylsilane with no ruthenium compound. The ruthenium compound employed in Examples 4 and 5, examples carried out according to this invention, employ triruthenium dodecacarbonyl. As shown in the examples, the synergistic combination of the ruthenium compound and the organosilicon compound provides an increase in the amount of methanol and ethylene glycol formed.

TABLE I

| Example | Ruthenium Compound | moles of Ru Compound | Pressure (psig) | Product (1 hour)[1] Methanol | Glycol[2] | Product (2 hours)[1] Methanol | Glycol[2] | Product (4 hours)[1] Methanol | Glycol[2] |
|---|---|---|---|---|---|---|---|---|---|
| 1 | — | — | 6000 | T[3] | — | 0.21 | 0.14 | 0.14 | 0.09 |
| 2 | — | — | 6300 | T | — | T | 0 | VS | 0 |
| 3 | — | — | 8000 | PT[3] | PT | VS[3] | PT | 0.23 | 0 |
| 4 | Ru$_3$(CO)$_{12}$ | 1.0 | 6000 | 1.6 | 0.32 | 2.2 | 0.54 | 3.3 | 0.52 |
| 5 | Ru$_3$(CO)$_{12}$ | 1.0 | 8000 | 1.4 | 0.41 | 2.1 | 0.59 | 3.9 | 0.64 |

[1] product is reported in grams and is not corrected for imcomplete derivatization.
[2] ethylene glycol
[3] PT = Perhaps Trace; T = Trace; VS = Very Small; and S = Small

EXAMPLES 6–8

Examples 6–8 are comparative examples carried out using no organosilicon compound with 1.0 millimole of triruthenium dodecacarbonyl at 270° C. for 4 hours using 80 ml solvent (shown in Table II) under 6000 psig of carbon monoxide and hydrogen (1:1 mole ratio).

TABLE II

| | | Product (4 hours)[1] | |
|---|---|---|---|
| Example | Solvent | Methanol | Glycol[2] |
| 6 | dibutyl ether | ~0.9 | Trace |
| 7 | tetraethylsilane[3] | ~0.8 | Trace |
| 8 | sulfolane | ~0.6 | Trace |

[1] given in grams
[2] ethylene glycol
[3] an organosilicon compound having no hydrogen bonded to silicon.

EXAMPLES 9 AND 10

Comparative examples 9 and 10, according to this invention, were carried out by reacting 50 ml of trihexylsilane at 270° C. for 4 hours under a pressure of carbon monoxide and hydrogen (1:1 mole ratio). Example 9 employs no ruthenium compound. Example 10 employs 0.63 millimole of triruthenium dodecacarbonyl. Examples 9 and 10 are set forth in Table III.

TABLE III

| | | Product (4 hours) | |
|---|---|---|---|
| Example | Pressure | Methanol | Glycol[1] |
| 9 | 4900 | 0.31 | 0 |
| 10 | 5000 | 3.2 | 0.35 |

[1] ethylene glycol

EXAMPLES 11–19

Comparative examples 11–19 were carried out by charging 80 milliliters of trihexylsilane and the metal catalyst shown in Table IV. The reaction was carried out under a carbon monoxide and hydrogen atmosphere (1:1 ratio of H$_2$:CO) under a pressure of 8000 psig for a period of 4 hours. Samples were tested at 1 hour, 2 hours and 4 hours after the reaction had begun. The results of comparative examples 11–19 are set forth in Table IV.

TABLE IV

| Example | Silane | Metal catalyst | mmoles of catalyst | Product (1 hr.)[1] | | Product (2 hrs)[1] | | Product (4 hrs)[1] | |
|---|---|---|---|---|---|---|---|---|---|
| | | | | MeOH | GLYCOL[2] | MeOH | GLYCOL[2] | MeOH | GLYCOL[2] |
| 11 | (C$_6$H$_{13}$)$_3$SiH | — | — | PT[6] | PT | VS[6] | PT | 0.23 | — |
| 12 | (C$_6$H$_{13}$)$_3$SiH | Rh(CO)$_2$acac[7] | 3.0 | 0.26 | 0.79 | 0.29 | 0.63 | 0.45 (0.5) | 0.50 (0.1) |
| 13 | (C$_6$H$_{13}$)$_3$SiH | ClRh(CO)(Ph$_3$P)$_2$[7] | 3 | ≦VS | — | 0.18 | — | 0.33 | — |
| 14[4] | (C$_6$H$_{13}$)$_3$SiH | Mn$_2$(CO)$_{10}$ | 1.5 | 0.28 | — | 0.18 | — | 0.38 | T[6] |
| 15[3] | (C$_6$H$_{13}$)$_3$SiH | Cu$_2$O | 1.5 | VS | — | 0.29 | — | 0.28 | T |
| 16[4] | (C$_6$H$_{13}$)$_3$SiH | H$_2$PtCl$_6$.6H$_2$O | 3 | S[6] | T | 0.18 | — | 0.14 | T |
| 17 | (C$_6$H$_{13}$)$_3$SiH | H$_2$OsCl$_6$.2H$_2$O | 3 | ND[5] | ND[5] | 0.85 | — | 0.31 | — |
| 18 | (C$_6$H$_{13}$)$_3$SiH | [Ph$_3$P]$_2$PdCl$_2$[7] | 3 | — | — | S | — | 0.28 | — |
| 19 | (C$_6$H$_{13}$)$_3$SiH | Co$_2$(CO)$_8$ | 1.5 | 0.38 | 0.62 | 0.49 | 0.76 | 0.56 (0.1) | 0.50 |

[1] given in grams and uncorrected for incomplete derivatization. Numbers in parentheses are additional amounts, not subject to correction, found in a small denser phase which accompanied the reaction mixture or in the acetone wash of the reactor.
[2] ethylene glycol
[3] copper plates the reactor
[4] gas evolved upon mixing at room temperature
[5] not determined
[6] PT = perhaps trace; T = trace; VS = very small; and S = small
[7] Ph$_3$P = triphenylphosphine; acac = acetonylacetonate

What is claimed is:

1. The process for making the products ethylene glycol, methanol, and derivatives thereof directly from the reaction of hydrogen and oxides of carbon which comprises carrying out said process in a liquid phase containing an effective amount of a ruthenium carbonyl catalyst and an organosilicon compound, having at least one hydrogen bonded to silicon, said process being carried out at a temperature between about 50° C. and 400° C. and a pressure between about 100 psia (7.0 Kg/cm$^2$) and 15,000 psia (1,054.6 Kg/cm).

2. The process of claim 1 wherein the temperature is between about 100° C. and about 350° C.

3. The process of claim 1 wherein the pressure is between about 500 psia (35.15 Kg/cm$^2$) and 12,500 psia (878.84 Kg/cm$^2$).

4. The process of claim 1 wherein the pressure is the total pressure of hydrogen and carbon monoxide supplied to said process.

5. The process of claim 1 wherein a solvent is employed in said liquid phase.

6. The process of claim 5 wherein unreacted carbon monoxide and hydrogen are recycled to the liquid phase.

7. The process of claim 1 wherein the amount of ruthenium carbonyl catalyst and organosilicon compound are each between about 10$^{-6}$ percent by weight and about 30 percent by weight.

8. The process of claim 1 wherein the organosilicon compound is an mono-, di-, or trialkylsilane.

9. The process of claim 8 wherein the organosilicon compound is a trialkylsilane.

10. The process of claim 1 wherein the organosilicon compound is a silicon derived polymer.

* * * * *

UNITED STATES PATENT AND TRADEMARK OFFICE
CERTIFICATE OF CORRECTION

PATENT NO. : 4,360,600
DATED : November 23, 1982
INVENTOR(S) : Leonard Kaplan and Robert G. Bergman It is certified that error appears in the above—identified patent and that said Letters Patent is hereby corrected as shown below:

At Col. 3, line 52 "et et." should read --et al.--.

At Col. 3, line 53 "has" should read --have--.

At Col. 3, line 54 "produce" should read --produces--.

At Col. 4, line 20 "systhesis" should read --synthesis--.

At Col. 4, line 35 "report" should read --reported--.

At Col. 6, line 47 "chenicals" should read --chemicals--.

At Col. 6, line 55 "carohydrates" should read --carbohydrates--.

At Col. 6, line 65 "pressure" should read --pressures--.

At Col. 7, line 23 "catlayst" should read --catalyst--.

At Col. 7, line 34 "organosilcon" should read --organosilicon--.

At Col. 8, line 8 "introducted" should read --introduced--.

At Col. 8, line 51 "othe" should read --other--.

At Col. 12, line 66 "effeciency" should read --efficiency--.

At Col. 13, line 16 "removal" should read --removable--.

UNITED STATES PATENT AND TRADEMARK OFFICE
CERTIFICATE OF CORRECTION

PATENT NO. : 4,360,600
DATED : November 23, 1982
INVENTOR(S) : Leonard Kaplan and Robert G. Bergman It is certified that error appears in the above—identified patent and that said Letters Patent is hereby corrected as shown below:

At Table 1, note 1 "imcomplete" should read --incomplete--.

At Col. 13, line 49 "$(n-C_6H_{13})_3 SiOCH_2OSi (n-C_6H_{13})_3$" should read $(n-C_6H_{13})_3SiOCH_2CH_2OSi(n-C_6H_{13})_3$.

At Col. 14, line 12, "employ" should read --was--.

Signed and Sealed this

Fifteenth Day of May 1984

[SEAL]

Attest:

GERALD J. MOSSINGHOFF

Attesting Officer

Commissioner of Patents and Trademarks